United States Patent [19]
Cromer, Jr. et al.

[11] Patent Number: 5,365,026
[45] Date of Patent: Nov. 15, 1994

[54] USER INTERFACE CONTROL APPARATUS

[76] Inventors: Jerry E. Cromer, Jr.; Jerry E. Crower, both of 119 McQueen St., Sumter, S.C. 29150

[21] Appl. No.: 51,562

[22] Filed: Apr. 23, 1993

[51] Int. Cl.⁵ .................. H01H 9/24; H01H 35/40; G09G 3/00
[52] U.S. Cl. ................ 200/1 R; 200/52 R; 200/837; 200/81.4; 340/825.19
[58] Field of Search .............. 200/1 R, 5 R, 17 R, 200/18, 52 R, 61.22, 61.25, 81 R, 81.4, 81.5, 83 Q, 837; 307/118; 340/573, 626, 825.19; 379/52; 400/87; 623/24, 26

[56] References Cited

U.S. PATENT DOCUMENTS

| | | | |
|---|---|---|---|
| 3,229,059 | 1/1966 | Beatty | 200/61.41 |
| 3,848,249 | 11/1974 | Meiri | 340/325 |
| 3,911,316 | 10/1975 | Feick et al. | 318/562 |
| 4,207,959 | 6/1980 | Youdin et al. | 180/167 |
| 4,298,863 | 11/1981 | Natitus et al. | 340/573 |
| 4,453,043 | 6/1984 | Zielinski et al. | 179/90 BD |
| 4,562,432 | 12/1985 | Sremac | 340/706 |
| 4,567,479 | 1/1986 | Boyd | 340/709 |
| 4,706,067 | 11/1987 | Hauck | 340/365 R |
| 4,746,913 | 5/1988 | Volta | 340/706 |
| 4,865,610 | 9/1989 | Muller | 623/24 |
| 4,871,154 | 10/1989 | Seney | 269/97 |
| 4,979,094 | 12/1990 | Gemmell et al. | 364/188 |
| 5,126,731 | 6/1992 | Cromer, Jr. et al. | 340/825.19 |

OTHER PUBLICATIONS

Proceedings of the Fourth Annual Conference on Systems and Devices for the Disabled, Jun. 1977, pp. 147-150 U.S.A. Today—Techtalk "Physical Therapy and a Mean Pinball", Aug. 2, 1990.

Primary Examiner—A. D. Pellinen
Assistant Examiner—Michael A. Friedhofer
Attorney, Agent, or Firm—Oliff & Berridge

[57] ABSTRACT

A user interface controller for use by physically challenged persons has multiple function capabilities to operate an electronic device such as a computer or video game system. The controller provides activation of a plurality of first type control devices through a first type movement of a mouthpiece actuator, selection of one or more banks of second type control devices through a second different type movement of the mouthpiece, and activation of one or more second control devices within a selected bank of second control devices through puff and sip operations performed through the mouthpiece.

20 Claims, 7 Drawing Sheets

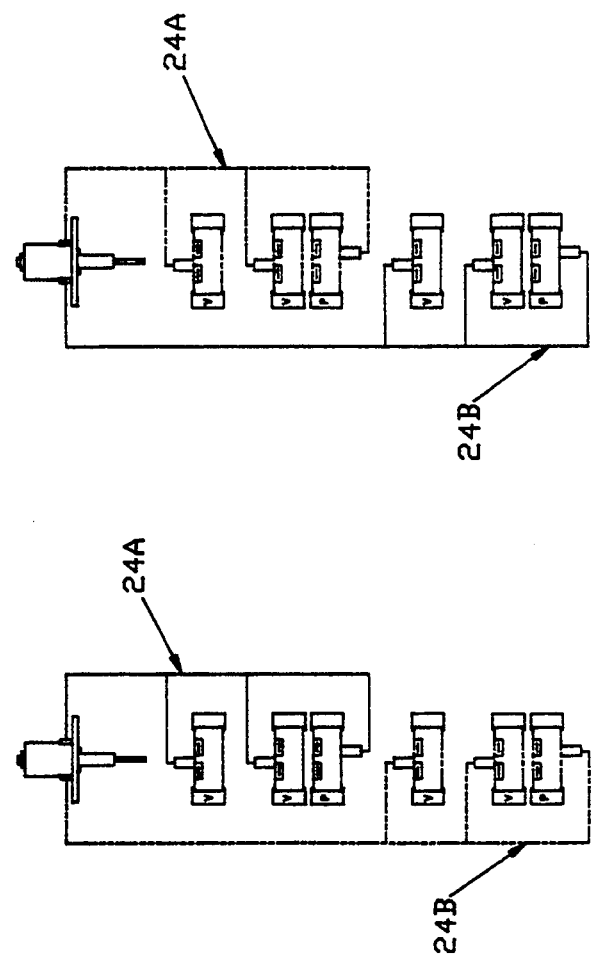
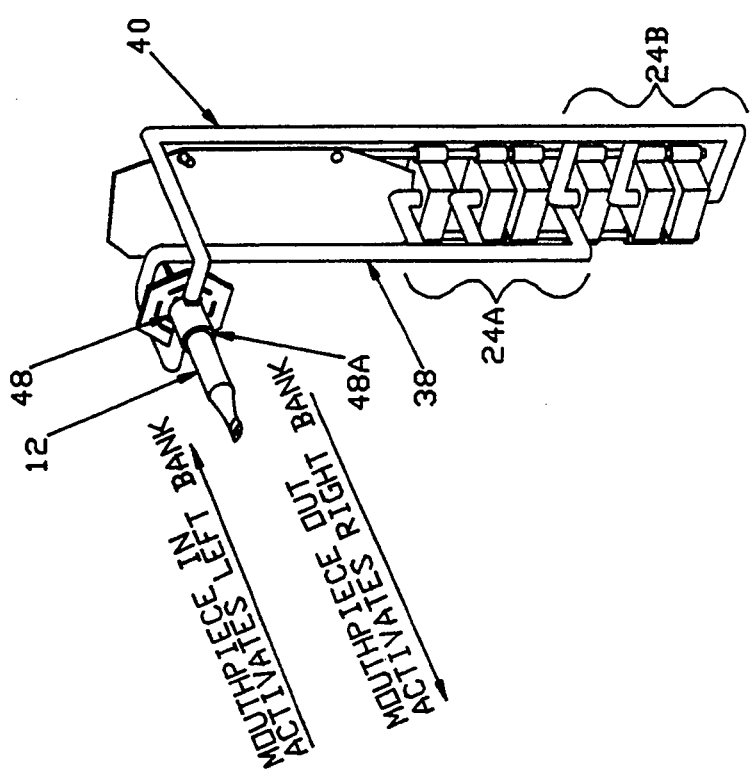
FIG. 3
FIG. 4
FIG. 5

USER INTERFACE CONTROL APPARATUS

BACKGROUND OF THE INVENTION

1. Field of the Invention

The invention relates generally to user interface control apparatus for use by physically challenged persons that has multiple functional capabilities to operate an electronic device such as a computer or video game system. More particularly, the invention relates to such control apparatus in which a plurality of control devices are selectively actuatable by a single mouth-operated actuator.

2. Description of Related Art

Several devices are known that interface with electronic devices to provide control thereof, such as a joystick, computer mouse, digitizer pad, and infrared remote controls. However, these are often difficult, if not impossible, to operate by a physically challenged person when multiple functions are necessary. For example, a conventional video game controller, such as for Super Nintendo, requires multiple functions to be performed simultaneously. This requires substantial hand and finger dexterity to operate separate controls simultaneously through use of a joystick type pad and a multiplicity of push buttons. This type of control is not suitable for a player who is severely physically challenged, such as a paraplegic or quadriplegic.

Numerous control devices are known for use by such physically challenged persons, including devices in which a switch interface includes both pneumatically actuated switches operated by a mouthpiece actuator and mechanically actuated switches. An example of such a control device, which was invented by the present inventor, is disclosed in U.S. Pat. No. 5,126,731. However, available controls can perform only a limited number of functions, cannot perform simultaneous functions and do not provide a great diversity of function capabilities.

There is thus a need for a user interface control device that is suitable for use by physically challenged persons and that can control various different electronic devices and perform multiple functions through the use of first and second actuated control devices such as switches. There also is a need for a control that can select between several banks of switches to perform different operations.

OBJECTS AND SUMMARY OF THE INVENTION

It is accordingly an object of the invention to provide a user interface controller for use by physically challenged persons that contains a plurality of control devices that are selectively actuatable through use of only a single actuator.

It is another object of the invention to provide a user interface controller for use by physically challenged persons that contains a plurality of mechanically actuated control devices and a plurality of pneumatically actuated controllers, all of which are selectively actuatable by a single mouthpiece actuator.

The above and other objects are achieved in accordance with the invention by providing an "air stick" user interface control apparatus in which a single mouthpiece actuator selects/controls a plurality of first control devices, such as switches, that are responsive to a first type of movement of the actuator; and selects one or more banks or arrays of pneumatically responsive second control devices through a second type of movement of the actuator. Puff and sip operations on the actuator control one or more of the second control devices within a selected bank of pneumatic switches.

In accordance with one aspect of the invention, the first control devices are selected and controlled through pivotal movement of the mouthpiece, the one or more banks of second control devices are selected through longitudinal push/pull axial movement of the mouthpiece, and the one or more second control devices within a selected bank of second control devices are selected and controlled through puff and sip operations performed through the mouthpiece.

In accordance with a further aspect of the invention, the control apparatus allows a physically challenged user to selectively simultaneously activate multiple function capabilities using a single mouthpiece actuator, through selected concurrent pivotal/longitudinal movement of and controlled air flow through the mouthpiece actuator. The control apparatus of the invention is thus particularly suited for use as a game controller to play video game systems, such as Super Nintendo, that require multiple functions to be simultaneously actuated.

A control apparatus according to the invention is capable of controlling, with only a single mouthpiece, a plurality of first control devices by pivoting the mouthpiece in different angular directions. Any suitable number of control devices can be utilized. For instanced six control devices, e.g., mechanical switches can be arranged in a radial fashion, at 60° intervals. Pivoting of the mouthpiece actuates one or more of the switches, causing a switching signal to be generated that controls an electronic device. Built-in air control responsive to air flow through the mouthpiece also permits a plurality of pneumatically actuatable control devices, e.g., pneumatic switches, to be controlled, and thus, multiple functions to be switched simultaneously and in conjunction with functions activated by the mechanical switches.

Further, the mouthpiece moves axially in a second type movement preferably along a longitudinal axis of the mouthpiece that also constitutes the pivot axis of the mouthpiece, to select one of a plurality of pneumatic switch banks or arrays. The mouthpiece is movable longitudinally between two or more positions. In a preferred embodiment, the mouthpiece is movable between "pushed in" and "pulled out" positions. When the mouthpiece is pushed in, a first bank of pneumatic switches is selected and individual switches therein are activated by controlling air flow through the mouthpiece actuator. When the mouthpiece is pulled out, air flow to the first bank is shut off, and air flow is controlled to a second bank of switches, thereby selecting the second bank and activating individual switches therein. This allows the same operation, on the mouthpiece, i.e., puffing or sipping, to activate different switches and perform different functions, depending on whether the mouthpiece is pulled out or pushed in.

Additionally, the individual pneumatically actuatable control devices can be respectively set to different levels of pressure or vacuum, thus allowing two or more control devices to be simultaneously activated. This can be accomplished when using pneumatic switches either by using switches having differing pressure sensitivity, or by providing air manifolds in the air flow paths, leading to each switch, which manifolds are adjustable to modify the air flow pressure input to the switch.

Advantageously, one or more of the switches is a latching form of switch, so that the switch maintains its switched state after being actuated until it is again actuated. Alternatively, one or more of the switches is connected to an associated latch circuit or circuits which similarly produce and maintain control outputs when actuated until they are again actuated.

The control apparatus can be adapted to per,form three or four operations simultaneously. At least one mechanically responsive control device can be activated through pivoting of the mouthpiece, while any number of operations or functions can be activated by one or more pneumatic switches.

The control apparatus fully adjusts in height to accommodate varying wheel chair or body height, and also adapts for a person in a reclining position. With six mechanical and six pneumatic control devices, multiple control functions are readily provided, and a person who is severely physically challenged thus can effectively, and competitively, operate electronic devices having complex control input requirements such as video games.

These and other objects, features and advantages of the invention are described in or apparent from the following detailed description of preferred embodiments.

BRIEF DESCRIPTION OF THE DRAWINGS

The preferred embodiments are described with reference to the following drawings wherein:

FIGS. 2-3 are partial perspective views of internal components of the control apparatus of FIG. 1;

FIGS. 4 and 5 are schematic diagrams showing activation of left and right banks of pneumatic switches by longitudinal movement of a mouthpiece according to the invention;

DETAILED DESCRIPTION OF PREFERRED EMBODIMENTS

Figure 1:
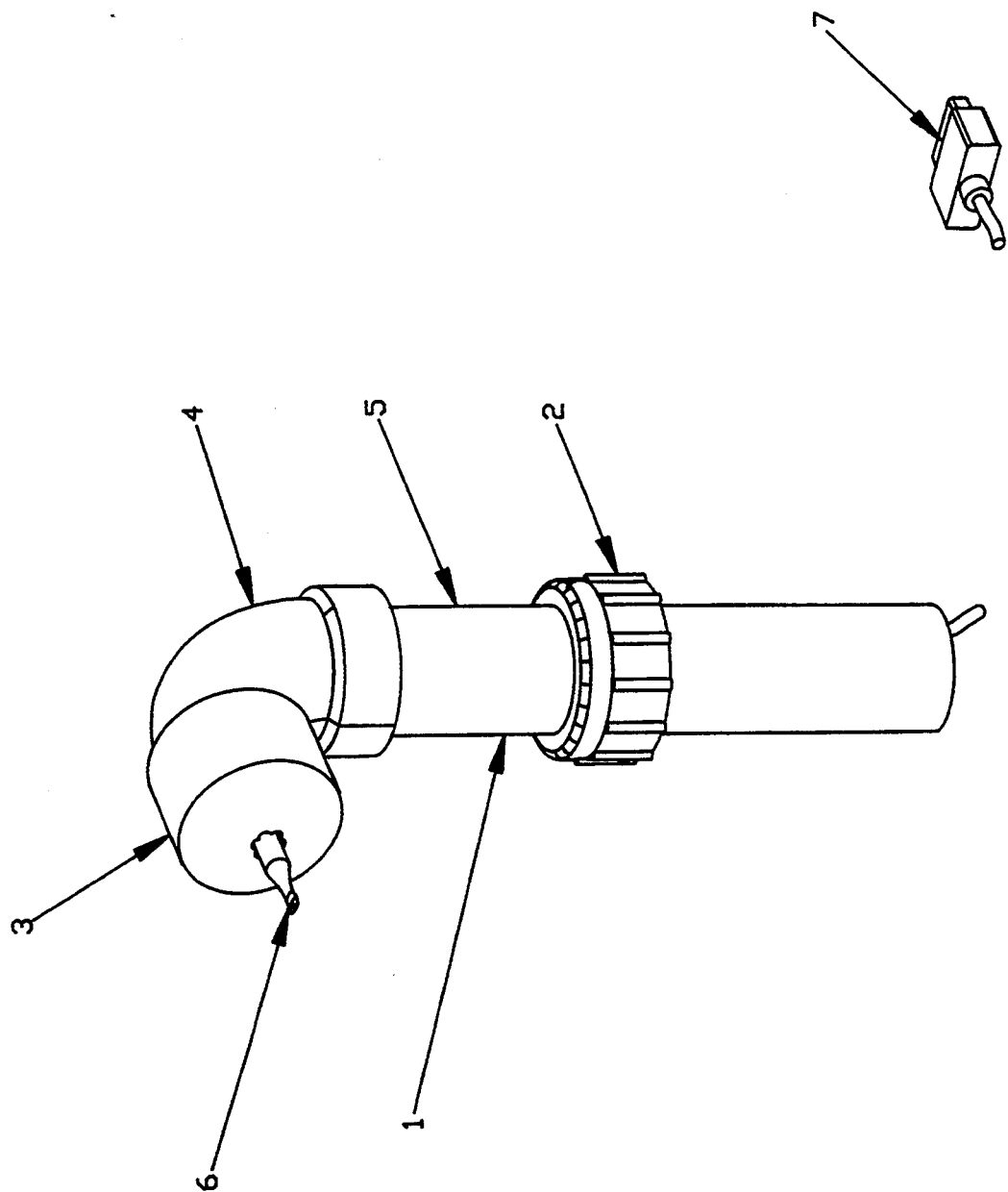
FIG. 1 is a perspective view of user interface control apparatus according to the invention.

Referring to FIG. 1, an "air stick" user interface controller 10 according to the invention, which can emulate and interface with various electrical devices, such as a computer, infrared sensors, or video game systems to provide selective activation of a plurality of functions with a single actuator, comprises a housing 18 which contains a control device actuator 14, a plurality of first control devices 16 responsive to movement of actuator 14, a plurality of pneumatically responsive second control devices 24, and a circuit board interconnector 26 (FIGS. 2-3) for electrically connecting the first and second control devices 16 and 24 to a multi-wire connecting cable 28 and plug 30. Plug 30 is adapted to be compatible with the input connection interface of the electrical device being controlled.

Housing 18 comprises a lower tubular base member 20, an upper 90° elbow member 22 mounted on base member 20, and a cap 42 mounted on the end of elbow member 22 and having an opening through which a mouthpiece 12 of actuator 14 extends. As shown, housing 18 is elongated and sized to completely house all of the pneumatic control devices 24 and associated components, while actuator 14 and control devices 16 are contained within cap 42. In the illustrated embodiment, which has six stacked pneumatic control devices 24, tube member 20 has a length L of 10 inches. It is understood that the housing size would vary depending on the size and number of control devices 24 and circuit board interconnector 26. Housing 18 is advantageously made from PVC piping. A PVC expansion nut 32 is slidably mounted on member 20 for mounting of controller 10 on a base (not shown), so that the height of mouthpiece 12 relative to the base can be adjusted. The base preferably pivotally adjustable to also provide angular adjustment of controller 10. Nut 32 may be internally threaded to accept a threaded tubular end of the base. Tightening nut 32 onto the threaded base end locks the controller 10 at any desired mouthpiece height.

In the disclosed embodiments, discrete mechanically and pneumatically actuated switches having two switch states are used as the first and second control devices 16 and 24, respectively. The invention, however, can also be practiced with other types of control devices which produce control outputs. For example, the control devices 16 advantageously may comprise electronic circuits producing at least one control output signal and having one or more trigger elements responsive to predetermined movement of actuator 14. Trigger elements, for example, can be responsive to engagement in response to movement of actuator 14, or can include magnetic, optical or other type sensors for sensing movement of actuator 14. Such control devices can produce two or more than two discrete output states, or can produce analog output signals having a characteristic that varies according to the relative position of mouthpiece 12 or the relative pressure produced by puffing or sipping on mouthpiece 12. The invention can also be practiced with integrated or monolithic forms of mechanical/electrical/pneumatic control devices wherein the individual control devices are formed as elements on a single substrate such as a printed circuit board.

In the disclosed embodiment, twelve switches (six mechanical switches and six pneumatic switches) can be actuated through operation of the single mouthpiece 12. Although twelve control circuits are preferred for such applications as video game control, applicants contemplate that any number of control circuits may be provided depending on the application.

Control switches 16 and 24 advantageously are normally open switches which remain closed only when actuated. Alternatively, one or more of switches 16 and 24 can be a latching-type switch, or connected to a latching relay or circuit (not shown), so that the switch/latching circuit remains in a switched activated state following initial actuation of the switch and until the switch is again actuated.

Actuator 14 controls the plurality of mechanical switches 16 with only single mouthpiece 12 by pivoting mouthpiece 12 relative to mechanical switches 16 and enables one or more banks of pneumatic switches 24 by longitudinal movement of mouthpiece 12 in an in or out direction. Once a bank of switches 24 is enabled, puff and sip operations on mouthpiece 12 control activation of one or more pneumatic switches 24 within the selected bank. Preferably, the mechanical switches 16 are selectively, individually actuatable by pivoting mouthpiece 12 to predetermined actuation positions, which in the enclosed embodiment with six switches 16, advantageously are angularly spaced at 60° increments. To provide positively defined actuation positions, the opening in cap 42 advantageously forms a cam 46 that has a scalloped surface forming detents 46a that function as seats at 60 degree increments so as to urge mouthpiece 12 toward an actuation position when mouthpiece 12 is pivoted in the general direction of the actuator. That is, mouthpiece 12 is retained by edges of the detents but is allowed pivotal movement in the recessed detents. It will be appreciated that actuator 14 can be adapted to actuate more than one switch 16 at a given actuation position.

Figure 9:
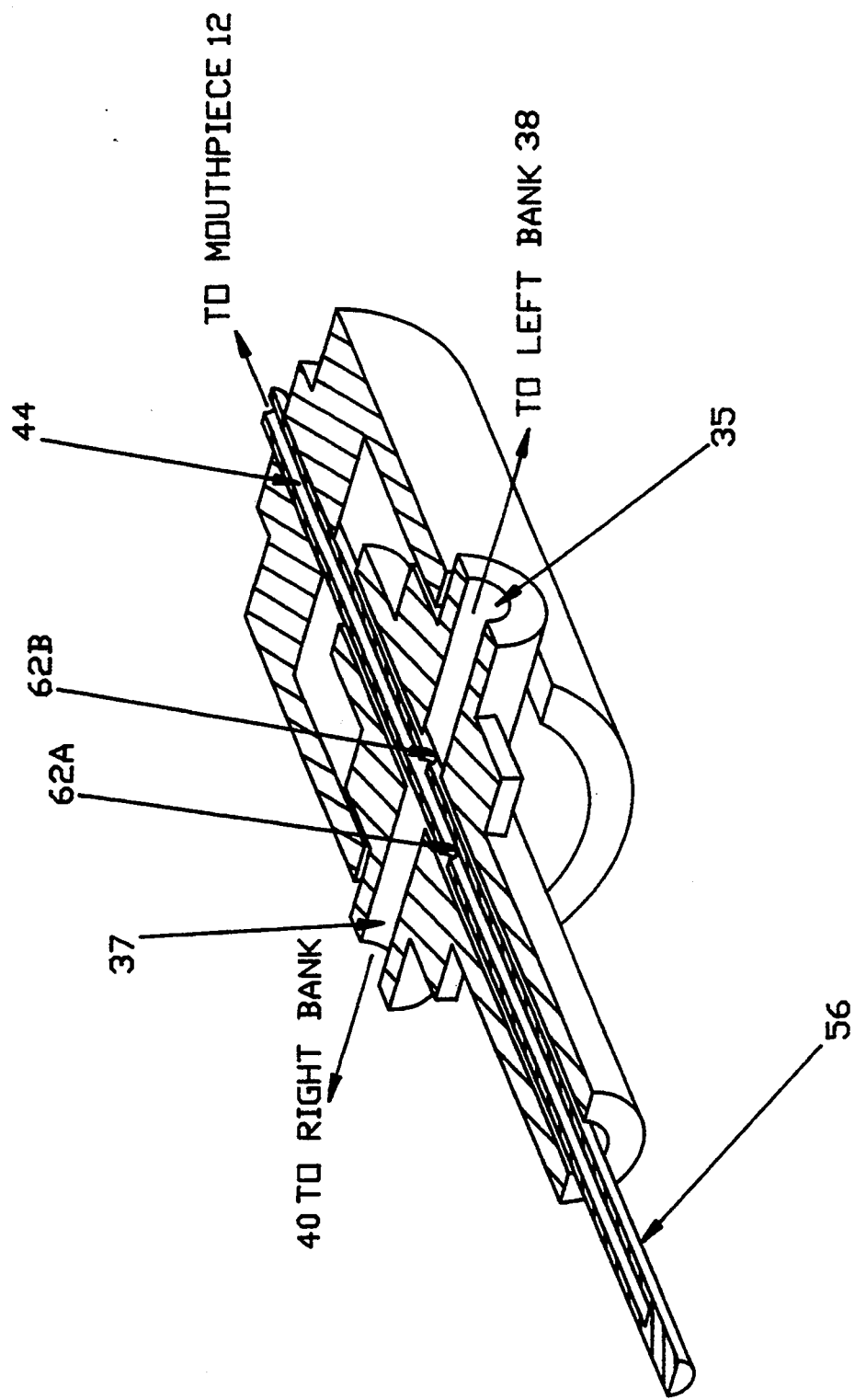
FIG. 9 is a partial cross-sectional view of a switch selecting manifold shown in FIG. 6.

Pneumatic switches 24 are grouped into a left bank 24a and a right bank 24b, each consisting of three pneumatic switches 24 connected in parallel with tubing defining associated air flow paths 38, 40 (FIG. 3). A pivot plate 48 (see FIG. 6) supports a manifold 49 to which the tubing defining air flow paths 38 and 40 are connected. Manifold 49 includes a hollow inner tube 56 that is movable longitudinally, and which can be similar to a syringe needle and made from stainless steel. Tube 56 forms an air passage 44, and mouthpiece 12 is airtightly, frictionally mounted in a projecting circular mounting collar 48a on pivot plate 48 (FIG. 3) that also receives a protruding portion of manifold 49 so that air passage 44 and tube 56 communicates with an air passage 45 in mouthpiece 12 (FIG. 9). It is also contemplated that O-rings may be provided in place of the frictional fit between mounting collar 48a and mouthpiece 12 to maintain an airtight seal between collar 48a and mouthpiece 12. Preferably, mouthpiece 12 is replaceable and includes a moisture filter.

Manifold 49 also includes left and right air passages 35 and 37 which communicate with air paths 38 and 40, respectively. Tube 56 further comprises at least two longitudinally spaced orifices 62 (FIG. 9) that also face in relatively opposite directions in the shown embodiment. When mouthpiece 12 is pulled out, orifice 62a lines up with air passage 37 to place switch bank 24b in fluid communication with mouthpiece airway passage 45, while left air flow path 38 is blocked from fluid communication with airway passage 45, i.e., the other orifice 62b does not line up with air passage 35 in this position. The opposite occurs when mouthpiece 12 is pushed in. Air flow path 38 is fluidly connected with air passage 45 via orifice 62b to enable or select left switch bank 24a, and right switch bank 24b is not enabled because the flow path via passage 37 is blocked.

More than the two shown positions may be provided, depending upon the application, to allow more than two different sets of functions (banks of control devices) to be selected through movement of mouthpiece 12 in the longitudinal direction. Any number of switches can be designated to each bank, although three are assigned to each bank in the shown embodiment. A preferred embodiment relies on frictional forces between tube 56 and manifold 49 to maintain the mouthpiece 12 at either of the two positions. Alternatively, mouthpiece 12 may be biased to a preferred or dominant one of the multiple positions. This can be accomplished by a suitable spring. Preferably, mouthpiece 12 has a ridge which releasably lockably engages with a mating feature inside of collar 48a. The frictional force is chosen to be high enough to hold the mouthpiece 12 in position, yet low enough that the user can easily overcome the force to remove the mouthpiece.

With reference to FIG. 3–5, when mouthpiece 12 is pushed in, left bank 24a of pneumatic switches 24 is selected and individual pneumatic switches 24 are activated by controlling air flow through left air flow path 38. When the mouthpiece 12 is pulled out, air flow to left bank 24a is shut off, while air flow is enabled to right air flow path 40, selecting right bank 24b, and individual pneumatic switches 24 of right bank 24b are controlled by the air flow through flow path 40. The right and left air flow paths 40, 38 may be formed of any suitable flexible or rigid tubing, e.g., flexible silicon or rubber tubing, or rigid PVC tubing.

As shown, pneumatic switches 24 can be pressure activated (positive pressure) or vacuum operated (negative pressure). Any desired combination of positive and negative pressure switches may be used in each switch bank. An important feature is that the pneumatic switches are pneumatically connected in parallel. As a consequence, one or more than one switch 24 in a selected bank can be selectively simultaneously activated by making respective ones of plural positive or negative pressure switches in the bank responsive to different pressure levels. For example, puffing (positive pressure) in the controller mouthpiece lightly at a first pressure will perform one control function by activating one switch 24; while puffing harder at a second pressure higher than the first pressure performs a different control function by actuating a predetermined combination of switches. Similar functions can be performed by sipping (vacuum) through mouthpiece 12.

Figure 2:
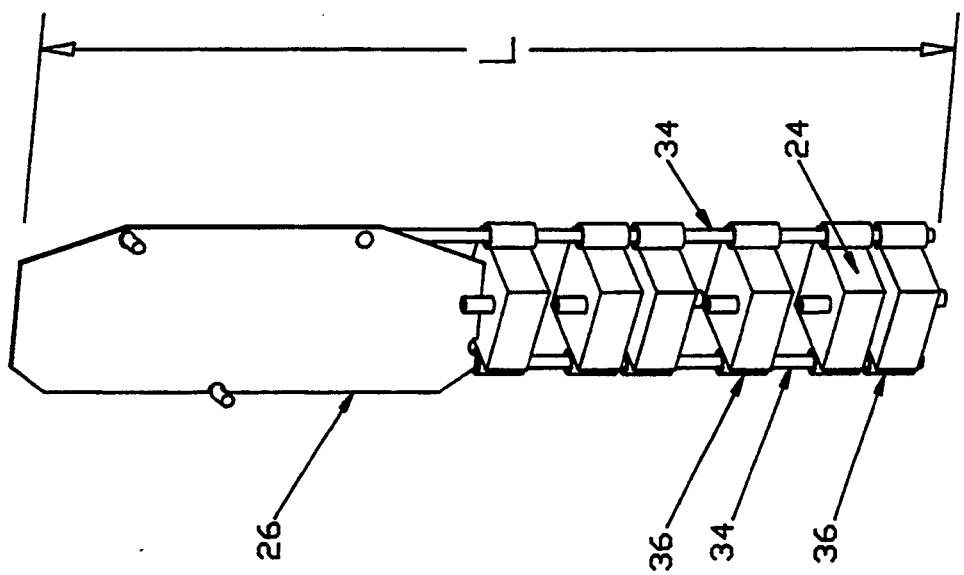

As shown in FIGS. 2–3, pneumatic switches 24 are provided in a stacked orientation, preferably vertical, and are fixedly held in place by a pair of rods 34 extending through circular mounting fixtures 36 located on pneumatic switches 24. Circuit board 26 is also preferably attached to rods 34. The orientation is preferably vertical to space controller mouthpiece 12 from a table or the like on which controller 10 is mounted at a height which is close to the mouth of the user. A vertical orientation also provides the user with a relatively unobstructed view around the controller. As previously discussed, housing 18 is configured so that the mouthpiece height is adjustable to accommodate different wheelchair or body heights, and so that controller 10 can be oriented for use by a person in a reclining position through use of a pivoting base.

Figure 6:
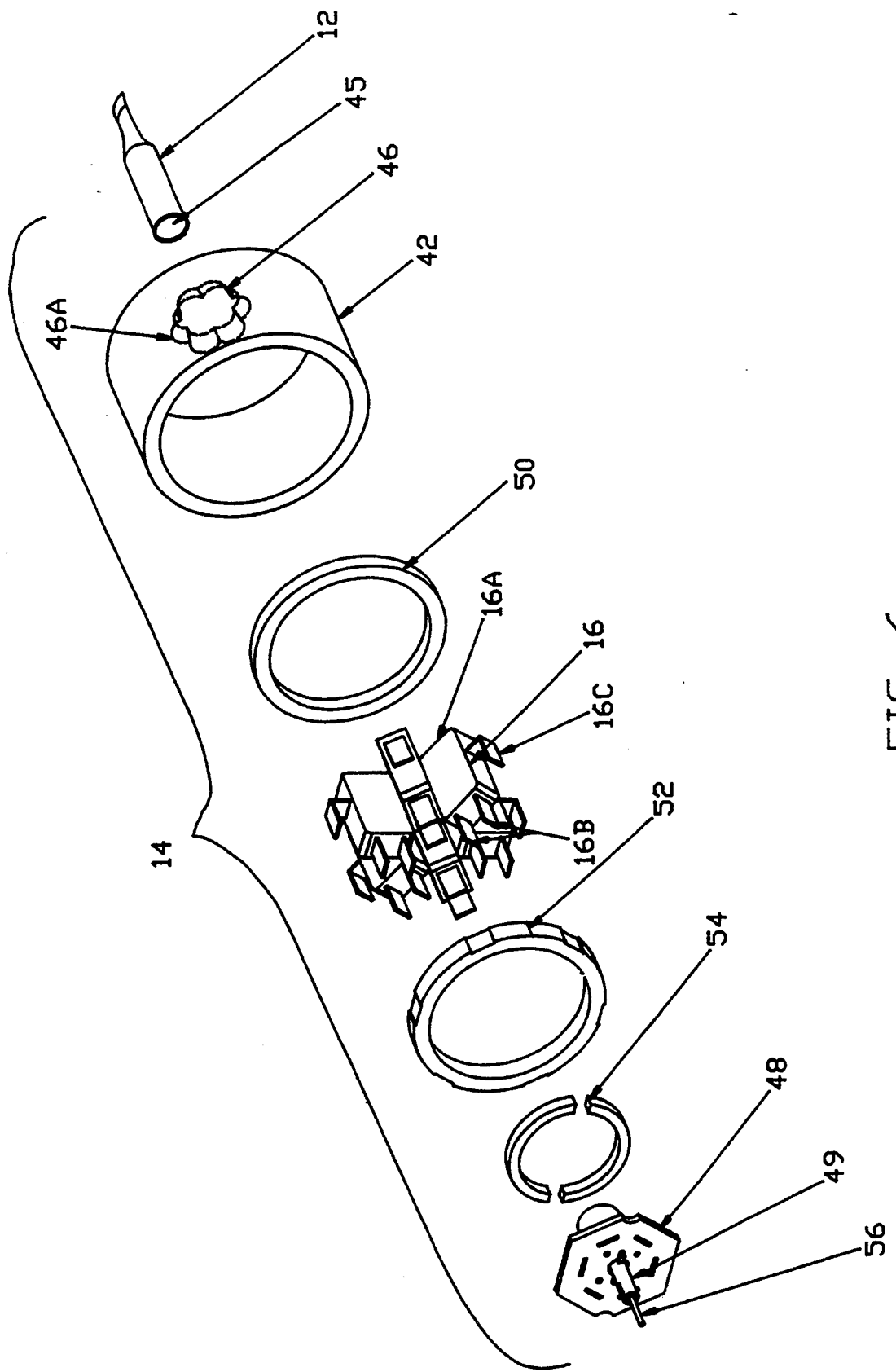
FIG. 6 is an exploded perspective view of further internal components of the user interface control apparatus.

Referring to FIG. 6, and also to FIGS. 1 and 4, a spacer ring 50 is fitted within cap 42 against the end of the cap through which mouthpiece 12 extends. Preferably, the spacer ring frictionally engages cap 42. An array of mechanical switches 16 are fixedly arranged in a radial pattern. Switches 16 are preferably standard microswitches having a rectangular housing 16a, a pair of spade terminals 16b, extending from one end face, a third spade terminal 16c extending from one side face, and an actuator element (not shown) at the side face opposite the face with terminal 16c. In the radial configuration, contacts 16c all face radially outward and the switch actuator elements all face radially inward towards mouthpiece 12. The mechanical switch array 16 is placed next to spacer ring 50. The thickness of spacing ring 50 can be adjusted to control the degree to which mouthpiece 12 must be pivoted to contact the actuating element of the mechanical switch 16. The thickness selected tends on the switches used and personal preference as to the feel of the actuator. A mounting ring 52 is then placed within cap 42 against mechanical switch array 16. Preferably, mounting ring 52 also frictionally engages cap 42, is electrically insulative, and includes notches which mate with and retain individual terminal 16c of microswitches 16 to prevent rotation of the mechanical radial array within cap 42. Spacer ring 50 also serves to retain the mechanical switch array 16 within cap 42 between mounting ring 52 and spacer ring 50. A split spacer ring 54 is then placed between switch terminals 16b. The splits in the split spacer ring 54 allow entry of left and right tubes forming air flow path 38 and 40 (see FIG. 9) for connection to manifold 49. Split spacer ring 54 also spaces pivot plate 48 from the remainder of the assembly. The pivot plate 48 may contain slots therein on a planar surface which mate with and receive terminals 16b of the microswitches. This complete assembly attaches to 90° elbow 22. Preferably, cap 42 and elbow 22 are non-threaded and attached by known adhesives to each other and also attached to tube member 20 forming housing 18 of controller 10.

An important advantage of the controller is that all switching and activation of functions can be operated through mouthpiece 12. In prior art, such as our prior U.S. Pat. No. 5,126,731, incorporated in its entirety herein, selection of function sets was accomplished through a rotatable switch separate from the mouthpiece. In the case of a severely challenged user, such as a paraplegic or quadriplegic, a caretaker is needed to operate the rotatable switch to change function sets. However, the present inventive controller allows full operation of multiple functions, selection between banks of function groups, and even actuating simultaneous functions, all through use of a single mouthpiece 12. Thus, no limbs or fingers are required to operate the device. This allows the controller to be fully operated by a physically challenged person, providing greater independence to the user and eliminating the need of a caretaker. The controller allows full control of complicated multiple function devices including video game systems, computers, or stereo systems.

Figure 7:
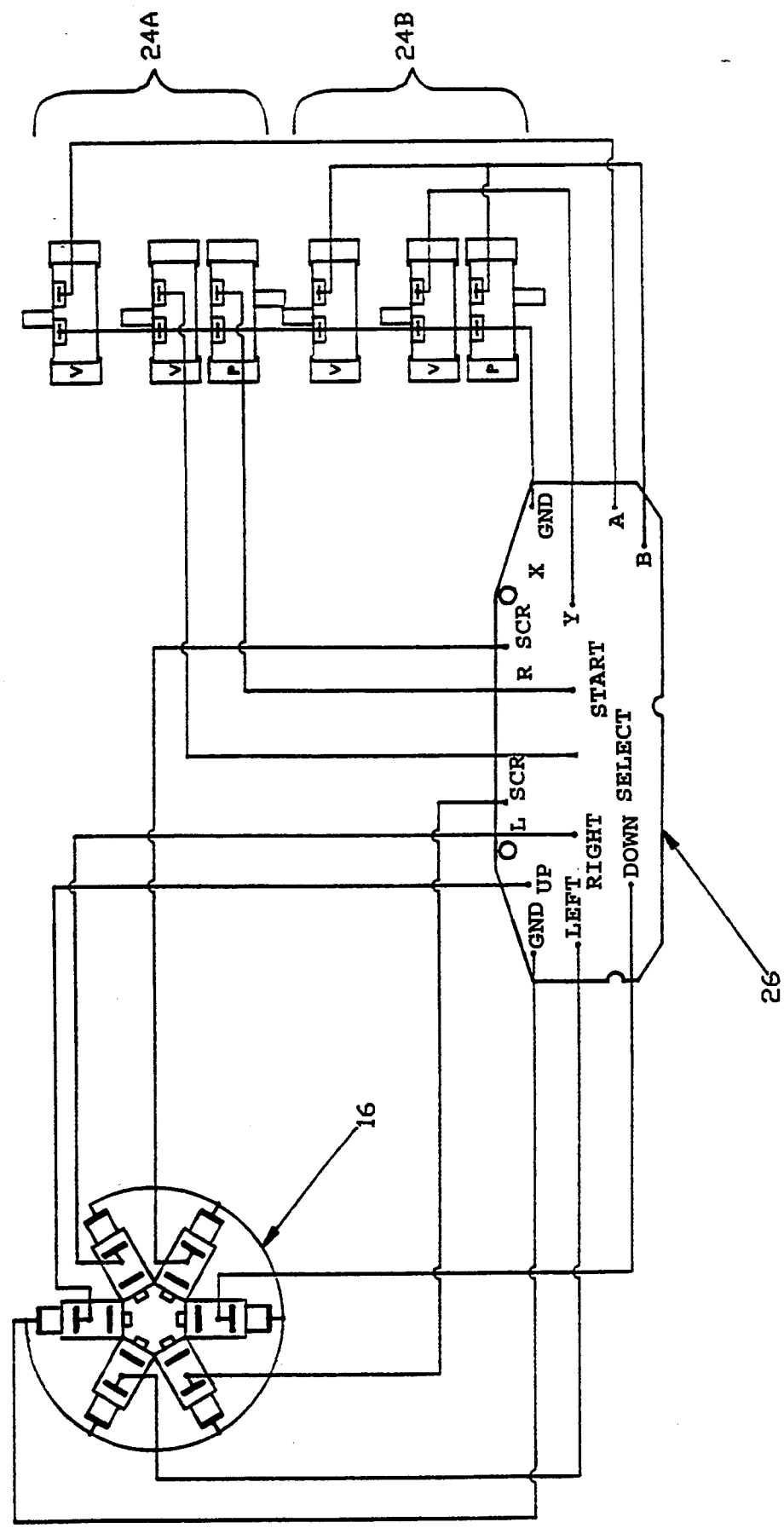
FIG. 7 is a schematic diagram showing electrical lead connections for a preferred embodiment emulating a Super Nintendo controller.

In an exemplary embodiment shown in FIG. 7, the controller 10 is electrically configured to operate a Super Nintendo game system. The schematic shows the wiring of the six mechanical switches 16 and six pneumatic switches 24 to circuit board 26 to operate all of the functions included in the Super Nintendo controller. A Super Nintendo standard controller requires use of one hand to operate directional control and one or more fingers from a second hand to operate push buttons. However, controller 10 allows all of these functions to be operated solely by mouth. As shown, the ten o'clock and two o'clock positions (of the mechanical switches) allow moving of the Super Nintendo screen. The twelve o'clock and six o'clock positions allow Mario to look up and to squat. The four o'clock and eight o'clock positions allow Mario to move left or right. All of these functions are controlled by pivotal movement of mouthpiece 12 about a pivot axis.

One contact of each of the six mechanical switches 16 and pneumatic switches 24 are connected to ground. The other contact is connected to an appropriate function. Pushing in of mouthpiece 12 to enable left bank 24a causes puffing and sipping operations on mouthpiece 12 to control the Super Nintendo select, start and A functions. Pulling out of mouthpiece 12 to enable right bank 24 causes puffing or sipping operations to activate the Super Nintendo Y and B functions.

Other configurations of switches 16 and 24 can be implemented to accommodate activation of any multiple function device which requires control. Examples of applications for which the controller is particularly suited are to control computer operations (turning on and off, operating mouse, and keyboard), or an infrared controller equipped to operate electronic devices such as a TV, VCR, or stereo system. The controller 10 is capable of selectively enabling and activating any of these devices using the same control operations. It will also be appreciated that one or more of the mechanical switches may be electrically interconnected with selected pneumatic switches as taught in our aforementioned U.S. Pat. No. 5,126,731 to permit the controller to be used with electrical devices having different input-/interface protocols.

Figure 8:
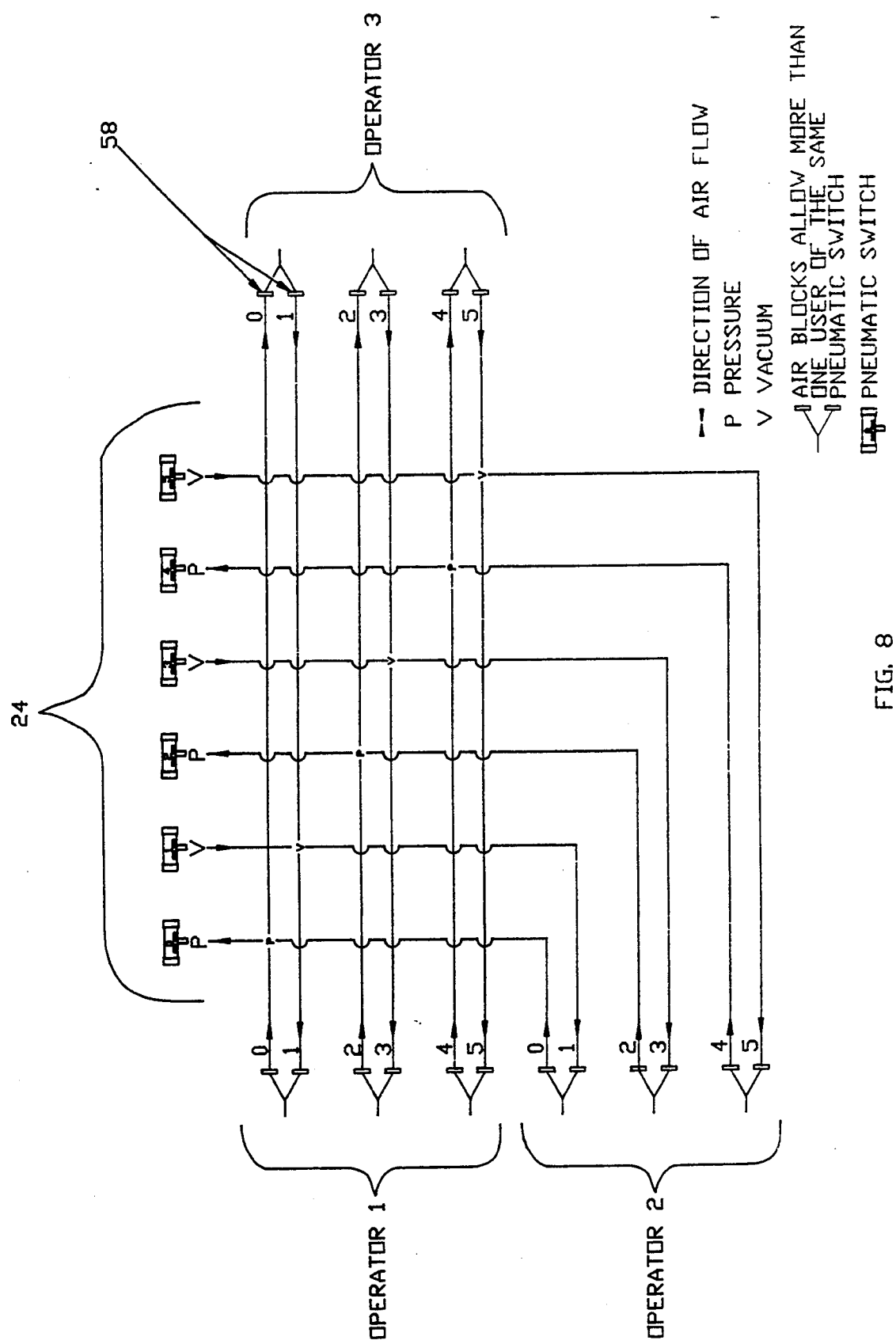
FIG. 8 is a schematic diagram showing a multi-user embodiment of user interface control apparatus according to the invention using air blocks to block air from one mouthpiece actuator from interfering with and entering an air path for other mouthpiece actuators associated with the device.

As shown in FIG. 8, numerous operators can utilize a single master unit (comprising the circuit board connections which plug into the electronic device and the pneumatic switches). Multiple controller mouthpieces having mechanically responsive switches can share the pneumatic switches. This saves on component requirements. The mouthpieces 12 are fluidly connected in parallel. In a preferred embodiment, air blocks 58 are provided which allow the first user who puffs or sips on his or her mouthpiece to operate the device while all other users are blocked from using the common airpath. The air blocks do not only prevent the other users from puffing or sipping into the device, but prevent air from the first user from entering the other users' mouthpiece. This provides safety and prevents contamination or spreading of germs from one user to the other. After the first user finishes a puffing or sipping operation, the next of the users that puffs or sips will have control of the device and sole access to the switches. The air blocks may comprise one way valves, similar to a reed switch, which allow air to flow one way, but not the other. Thus, many different users can operate the device. This would be useful where the controllers are used in conjunction with training or where a device such as a TV or computer accessed by numerous people is controlled. Each person can have a controller having a mouthpiece located near them which can operate the device. This would be particularly suited to a classroom or a common activity area in a building with a plurality of persons.

The invention has been described with reference to the preferred embodiments thereof, which are illustrative and not limiting. Various changes may be made without departing from the spirit and scope of the invention as defined in the appended claims.

What is claimed is:

1. A user interface controller for use by physically challenged users to selectively provide electrical control signals for operation of an electronic device, comprising:
   a plurality of first control devices;
   a plurality of pneumatically responsive second control devices;
   and a single actuator operatively connected to said first and second control devices so as to select predetermined ones of said first and second control devices for actuation by movement of the actuator.

2. The controller of claim 1, wherein the predetermined ones of said first control devices are selected by a first type of movement of said actuator and predetermined ones of said second control devices are selected by a second type of movement different from said first type of movement.

3. The controller of claim 2, wherein said first type of movement is pivotal and said second type of movement is axial.

4. The controller of claim 1, wherein said first and second control devices are switches electrically connected with inputs of the electrical device such that at least one control signal is produced responsive to switch actuation.

5. The controller of claim 1, wherein said actuator comprises a mouthpiece pivotally movable relative to a pivot axis to actuate said first control devices.

6. The controller of claim 5, wherein said first control devices comprise a plurality of mechanically actuated switches radially spaced about the pivot axis.

7. The controller of claim 2, wherein said first type of actuator movement is controlled by a cam defining predetermined directions of actuation movement, 8. The controller of claim 7, wherein said actuator comprises a mouthpiece mounted in a housing for pivotal movement relative to an axis of movement for said second type of actuator movement, and said cam is formed by a shaped opening in said housing through which said mouthpiece extends.

9. The controller of claim 5, wherein predetermined banks of said second control devices are selectively enabled through axial movement of said mouthpiece along said pivot axis.

10. The controller of claim 9, wherein each bank of second control devices fluidly communicates with said mouthpiece via an air flow path including a manifold controllable by said axial movement of said mouthpiece.

11. The controller of claim 10 wherein said manifold includes spaced air passages respectively connected to a corresponding one of the air flow paths for the banks of second control devices, and a moveable, orifice-containing member in fluid communication with said mouthpiece and responsive to said mouthpiece axial movement to position a predetermined orifice in fluid communication with a predetermined manifold air passage in dependence on the relative axial position of said mouthpiece.

12. The controller of claim 1, wherein a puffing operation performed through said mouthpiece activates at least one of said pneumatic control devices.

13. The controller of claim 1, wherein a sipping operation through said mouthpiece activates at least one of said pneumatic control devices.

14. The controller of claim 1, wherein the relative degree of pneumatic pressure, created by a user sipping or puffing air through said mouthpiece, selectively actuates at least one of said pneumatic switches.

15. The controller of claim 1, wherein a bank of pneumatic switches comprises two or more individual pneumatic control devices responsive to different pneumatic pressures.

16. The controller of claim 15, wherein a first predetermined air pressure activates one of said second control devices and a second predetermined air pressure greater than said first pressure activates two or more second control devices simultaneously.

17. The controller of claim 1, wherein said second control devices comprise discrete individual pneumatic switches.

18. The controller of claim 17, wherein said pneumatic switches are fixedly mounted in a stacked arrangement.

19. The controller of claim 18, wherein said individual pneumatic switches are fluidly connected so as to define at least two independently controllable banks of pneumatic switches, the individual pneumatic switches in each bank being fluidly connected in parallel with a common air flow path.

20. A user interface control system for use by multiple physically challenged users to selectively provide electrical control signals for operation of an electrical control device comprising at least two user interface controllers as recited in claim 1, wherein said controllers all share the same second control devices, and the mouthpiece of each controller fluidly communicates with the second control devices via an air block so that passage of air from one mouthpiece to another mouthpiece, and simultaneous actuation of second control devices by more than one mouthpiece are prevented.

* * * * *

UNITED STATES PATENT AND TRADEMARK OFFICE
CERTIFICATE OF CORRECTION

PATENT NO. : 5,365,026

DATED : November 15, 1994

INVENTOR(S) : Cromer, Jr. et al

It is certified that error appears in the above-indentified patent and that said Letters Patent is hereby corrected as shown below:

On the title page item [76], the second inventor's last name should read --Cromer--.

Signed and Sealed this

Twenty-fifth Day of April, 1995

Attest:

BRUCE LEHMAN

*Attesting Officer*  *Commissioner of Patents and Trademarks*